(12) United States Patent
Ozawa et al.

(10) Patent No.: US 7,736,481 B2
(45) Date of Patent: Jun. 15, 2010

(54) ELECTROPHORESIS DEVICE AND ELECTROPHORESIS METHOD

(75) Inventors: Miho Ozawa, Abiko (JP); Ryoji Inaba, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 62 days.

(21) Appl. No.: 12/071,835

(22) Filed: Feb. 27, 2008

(65) Prior Publication Data

US 2008/0202932 A1 Aug. 28, 2008

(30) Foreign Application Priority Data

Feb. 28, 2007 (JP) ............................. 2007-048368

(51) Int. Cl.
  *G01N 27/453* (2006.01)
  *G01N 27/447* (2006.01)

(52) U.S. Cl. ...................................... 204/451; 204/601

(58) Field of Classification Search ......... 204/451–455, 204/601–605

See application file for complete search history.

(56) References Cited

U.S. PATENT DOCUMENTS

| 2,776,208 | A | | 1/1957 | Avery et al. |
| 3,519,647 | A | | 7/1970 | Krapcho |
| 5,582,705 | A | * | 12/1996 | Yeung et al. ................. 204/603 |
| 7,014,746 | B2 | * | 3/2006 | Maeshima et al. ........... 204/601 |

FOREIGN PATENT DOCUMENTS

| JP | 06-138037 A2 | 5/1994 |
| JP | 2776208 | 7/1998 |
| JP | 2001-099813 A2 | 4/2001 |
| JP | 2001-124736 | 5/2001 |
| JP | 2003-166976 | 6/2003 |
| JP | 3519647 | 4/2004 |
| JP | 3896739 | 1/2007 |

OTHER PUBLICATIONS

English language computer translation of Yoshio et al. JP 2003-166976 A, published Jun. 13, 2003.*

* cited by examiner

*Primary Examiner*—Alex Noguerola
(74) *Attorney, Agent, or Firm*—McDermott Will & Emery LLP

(57) ABSTRACT

To reduce the elongation of the migration time for the first electrophoresis cycle in successive electrophoresis cycles and improve the reliability of electrophoresis analysis. The present invention relates to making the condition of a migration medium at the start of the first electrophoresis analysis in successive electrophoresis analyses after the temperature in a thermostatic oven reaches a desired preset temperature substantially the same as the conditions after the successive electrophoresis analyses. Preferably, a voltage is applied to a separation medium filling a capillary during preheating of the thermostatic oven. Preferably, the temperature in the thermostatic oven during preheating is set higher than the temperature in the thermostatic oven during electrophoresis analysis. Preferably, a buffer solution is heated during preheating of the thermostatic oven. Preferably, the capillary is filled with a preheated separation medium during preheating of the thermostatic oven. According to the present invention, the reliability of the first electrophoresis analysis in successive electrophoresis analyses is improved.

5 Claims, 6 Drawing Sheets

FIG. 5
(A)
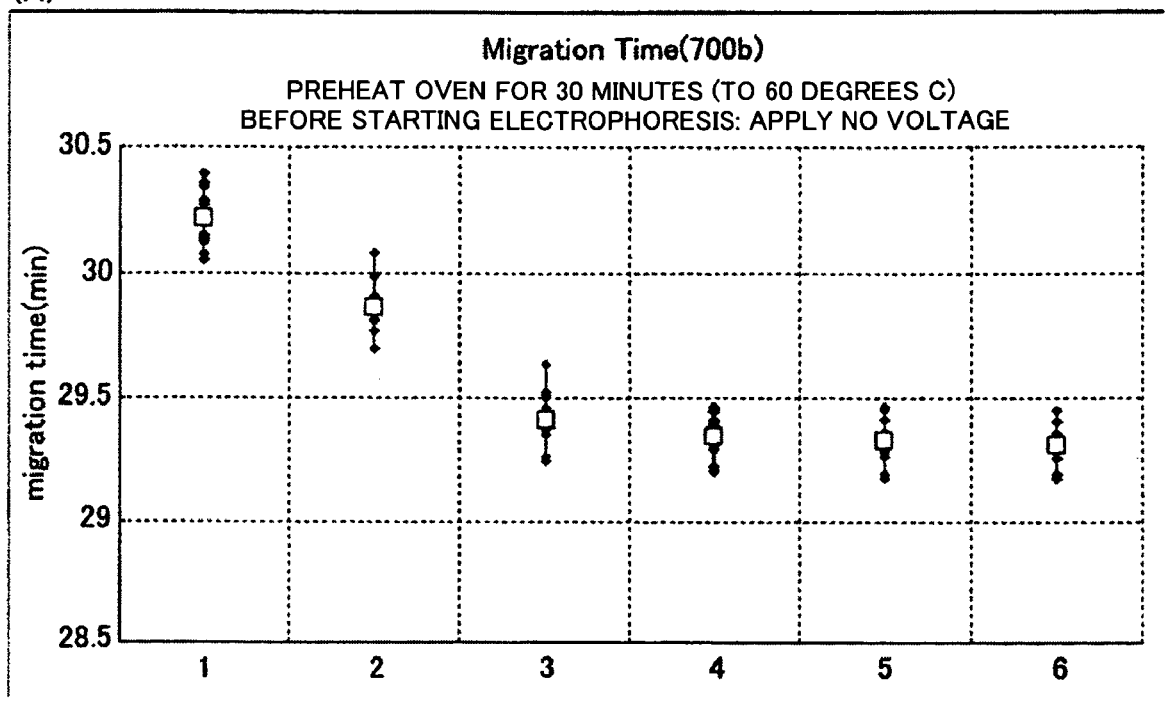
(B)
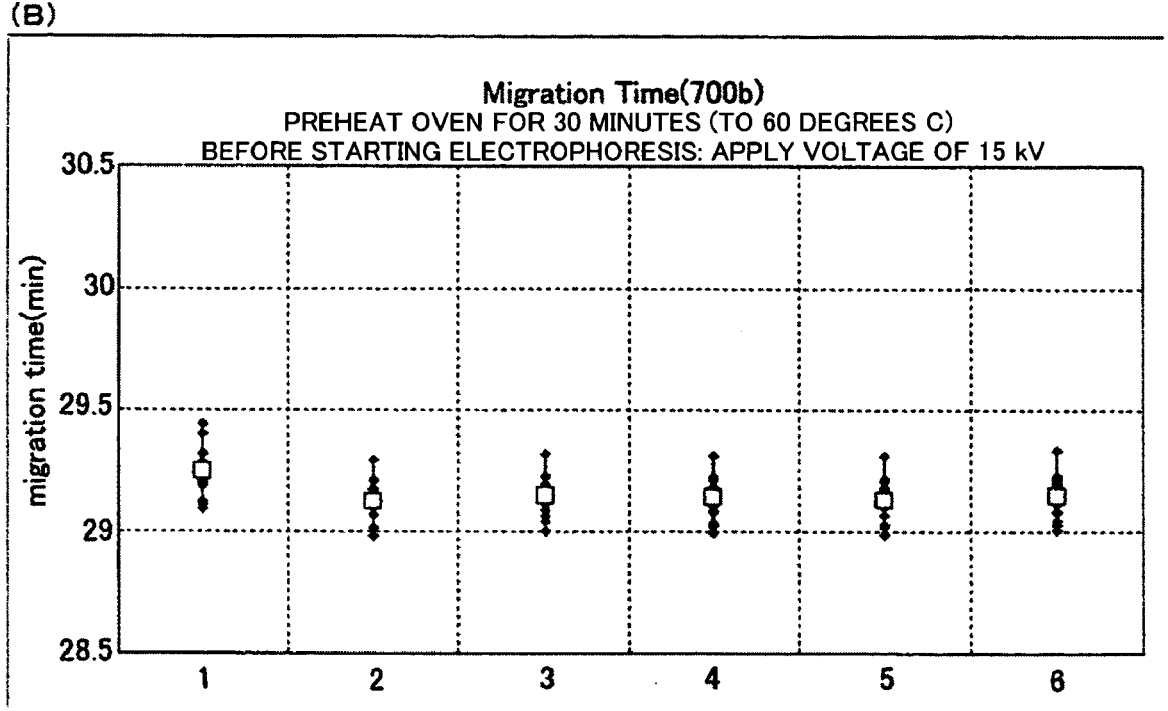

ELECTROPHORESIS DEVICE AND ELECTROPHORESIS METHOD

BACKGROUND OF THE INVENTION

1. Field of the Invention

The present invention relates to a technique of separating and analyzing constituents of a sample using capillary electrophoresis.

2. Background Art

In recent years, capillary electrophoresis devices having a capillary filled with an electrophoresis medium (separation medium), such as polymer gel and polymer solution, have become popular (JP Patent No. 2776208). Compared with a conventional slab gel electrophoresis device, a capillary electrophoresis device has a high radiation performance, can apply a high voltage and, therefore, can achieve high speed electrophoresis. Furthermore, the capillary electrophoresis device has many advantages that the amount of the sample is minute, that the capillary can be automatically filled with the separation medium, and that the sample can be automatically injected, for example. Thus, the capillary electrophoresis device is used for a wide variety of separation and analysis applications, including analysis of DNA and proteins.

In addition, JP Patent No. 3519647 discloses a DNA sequencer using capillary electrophoresis. In this specification, there is disclosed a thermostatic oven for adjusting the temperature of a plurality of capillaries. The device has a mechanism for filling a capillary with a polymer using a syringe or pump and a mechanism for performing automatic sample injection in the capillary or the like.

SUMMARY OF THE INVENTION

Conventional capillary electrophoresis devices can only provide unreliable electrophoresis data for the first electrophoresis cycle in successive electrophoresis cycles. In some cases, the data for the first electrophoresis cycle is unusable and discarded. In this regard, the present inventor has found the following as a result of earnest investigations.

The temperature in the thermostatic oven has not reached the temperature suitable for electrophoresis immediately after a capillary electrophoresis device is activated. Thus, to start an electrophoresis cycle, it is necessary to preheat the thermostatic oven and wait for the temperature in the thermostatic over to reach a temperature suitable for an intended application. Typically, after the operator conducts the operation to start an electrophoresis cycle, the entire process is suspended until the temperature in the thermostatic oven rises to fall within a desired temperature range. Once the temperature in the thermostatic oven falls within the desired temperature range, the process is resumed. The process is controlled by a controller based on the monitored temperature in the thermostatic oven.

However, even when the electrophoresis cycle is started after the temperature in the thermostatic oven reaches the desired preset temperature, the migration speed for the first cycle is lower than that for the second and the following cycles. This is because the temperature of the capillary rises because of the Joule heat produced by itself when a voltage is applied to the capillary, and therefore, in the first electrophoresis cycle, the temperatures of the capillary and the buffer have not reached the steady temperature, which is reached after a succession of electrophoresis cycles or after a voltage is continuously applied to the capillary, although the temperature in the thermostatic oven has become steady. Since the migration speed is lower in the first electrophoresis cycle, the electrophoresis data for the first cycle is less reliable and thus may be unusable and have to be discarded depending on the application.

An object of the present invention is to reduce the reduction of the migration speed for the first electrophoresis cycle in successive electrophoresis cycles and improve the reliability of electrophoresis analysis.

The present invention relates to making the condition of a migration medium or a migration buffer at the start of an electrophoresis analysis after the temperature in a thermostatic oven reaches a desired preset temperature substantially the same as the conditions after successive electrophoresis analyses.

Preferably, a voltage is applied to a separation medium filling a capillary during preheating of the thermostatic oven.

Preferably, the temperature in the thermostatic oven during preheating is set higher than the temperature in the thermostatic oven during electrophoresis analysis.

Preferably, a buffer solution is heated during preheating of the thermostatic oven.

Preferably, the capillary is filled with a preheated separation medium during preheating of the thermostatic oven.

According to the present invention, the reliability of the first electrophoresis analysis in successive electrophoresis analyses is improved.

BRIEF DESCRIPTION OF THE DRAWINGS

FIG. 5 includes graphs showing the migration time for successive electrophoresis cycles according to the embodiment 1.

DETAILED DESCRIPTION OF THE PREFERRED EMBODIMENTS

In the following, the above-described and other novel characteristics and advantages of the present invention will be described with reference to the drawings. The drawings are only for illustrative purposes and do not limit the scope of the present invention in any sense.

Figure 1:
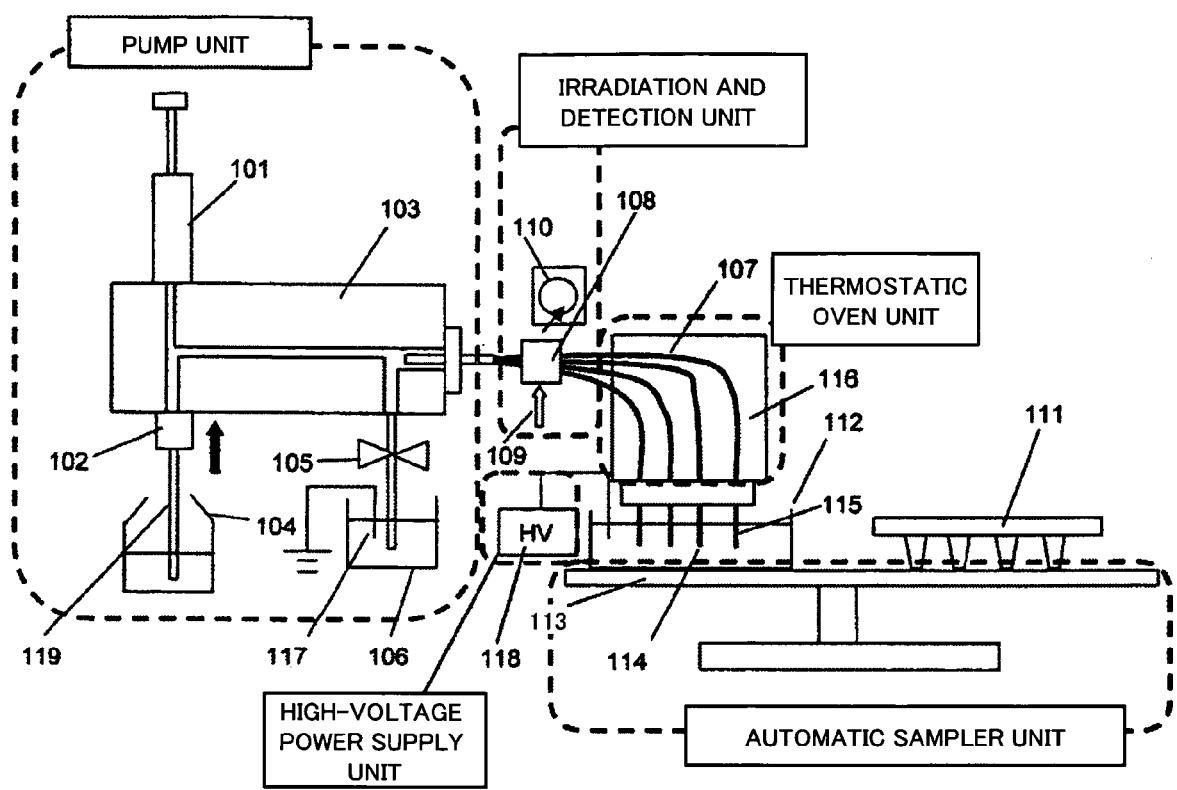
FIG. 1 is a schematic diagram showing a capillary electrophoresis device.

FIG. 1 is a diagram showing a basic configuration of a capillary electrophoresis device.

In terms of functionality, the device comprises a capillary capable of being filled with a separation medium, a thermostatic oven that houses at least a part of the capillary and adjusts the temperature of the capillary, a power supply mechanism capable of applying a voltage at least between the opposite ends of the capillary, a buffer reservoir that retains a buffer solution in which one of the capillary ends is immersed, and a separation medium filling mechanism capable of filling the capillary with the separation medium.

More specifically, the device further comprises a pump unit that fills the capillary with the separation medium, such as a polymer, an irradiation and detection unit that irradiates the capillary with light from a light source, such as a laser and an LED, and detects fluorescent light or the like emitted by the capillary, and a thermostatic oven unit that keeps the temperature of the capillary constant. The device further comprises an automatic sampler unit that conveys a sample tray from which a sample is distributed into sample injection ends of capillaries, the buffer reservoir that retains the buffer solution containing an electrolyte dissolved therein, a cleaning water reservoir that retains cleaning water for cleaning the tips of the capillaries, and a waste solution reservoir that retains a waste solution, which is the used separation medium discharged from the capillaries, to the sample injection ends of the capillaries.

Figure 2:
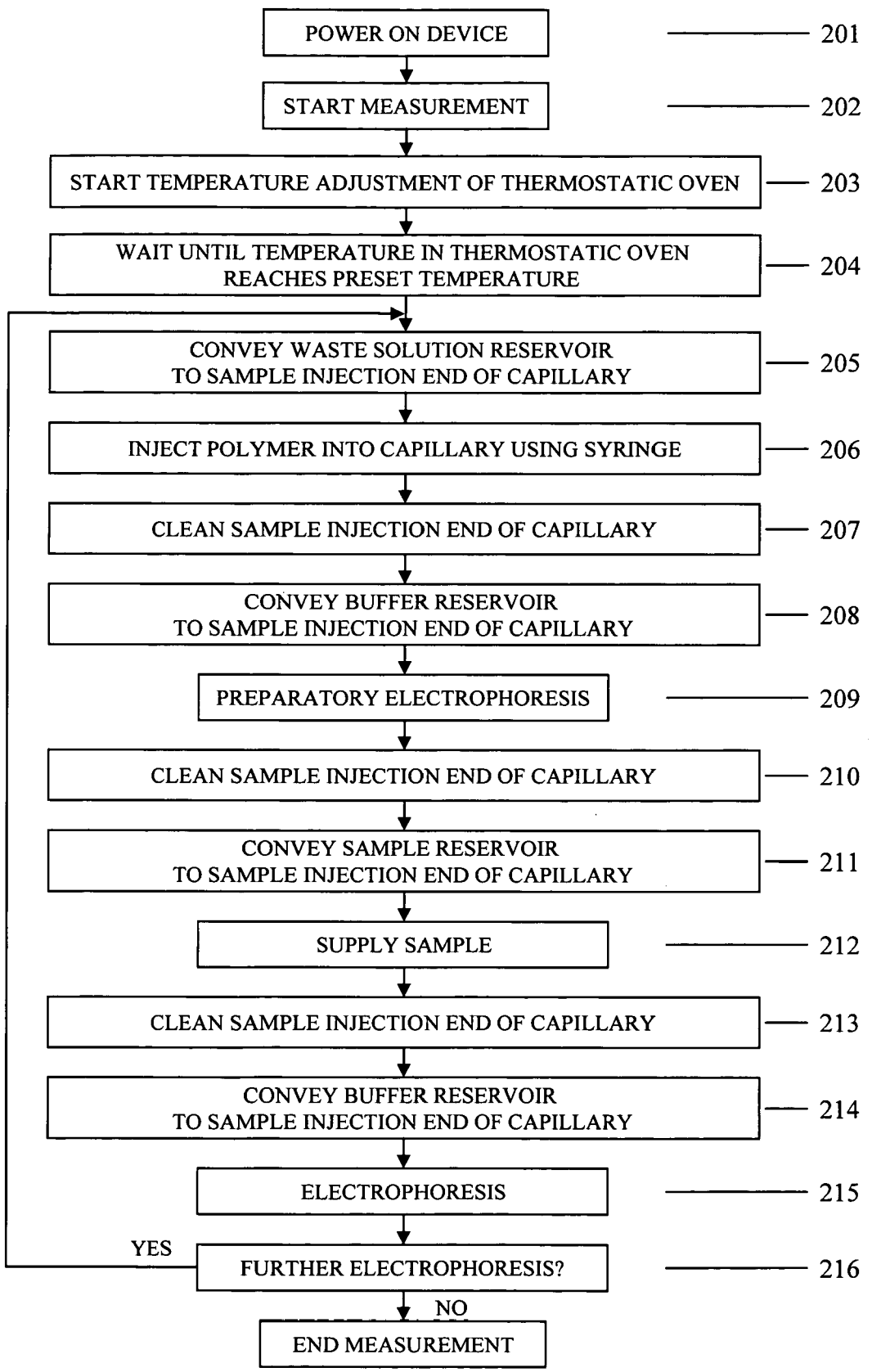
FIG. 2 is a flowchart showing a basic operation of the capillary electrophoresis device.

FIG. 2 is a flowchart showing a basic operation of the capillary electrophoresis device. The device is activated (201), and the measurement is started (202). Then, first, the temperature in the thermostatic oven housing the capillary is set, and the temperature adjustment is started (203). The process is suspended and not resumed until the temperature in the thermostatic oven reaches a steady temperature (204). When the temperature of the capillary reaches a preset temperature, an automatic sampler 113 conveys the waste solution reservoir that contains water in which the waste separation medium discharged from the capillary is to be dissolved to a sample injection end 114 of the capillary (205), and a fresh separation medium is injected into the capillary to force the used separation medium into the waste solution reservoir by using a syringe 101 (206). When the injection is completed, the automatic sampler 113 conveys the cleaning water reservoir to the sample injection end 114 of the capillary, and the sample injection end 114 of the capillary is cleaned in the cleaning water (207). Then, the automatic sampler 113 conveys the buffer reservoir to the sample injection end 114 of the capillary (208). Then, a voltage is applied to the capillary with no sample injected into to conduct preparatory electrophoresis (209). The automatic sampler 113 supplies the cleaning water to the sample injection end 114 of the capillary to clean the sample injection end 114 of the capillary (210). Then, the automatic sampler 113 conveys a sample reservoir to the sample injection end 114 of the capillary, and the sample injection end 114 of the capillary is immersed into a sample solution in the sample reservoir (211). A voltage is applied to the capillary to electrodynamically inject the sample into the capillary (212). The automatic sampler 113 supplies the cleaning water to the sample injection end 114 of the capillary to clean the sample injection end 114 of the capillary (213). Then, the automatic sampler 113 conveys the buffer reservoir to the sample injection end 114 of the capillary (214). An electrophoresis voltage is applied to the capillary to make an electrophoresis occur (215). When the electrophoresis is completed, it is determined whether a further electrophoresis is to be conducted. If a further electrophoresis is to be conducted, the waste solution reservoir is conveyed to the capillary (205), the capillary is filled with the polymer, and the steps for conducting an electrophoresis described above are conducted. If a further electrophoresis is not to be conducted, the electrophoresis process is ended.

Embodiment 1

Figure 3:
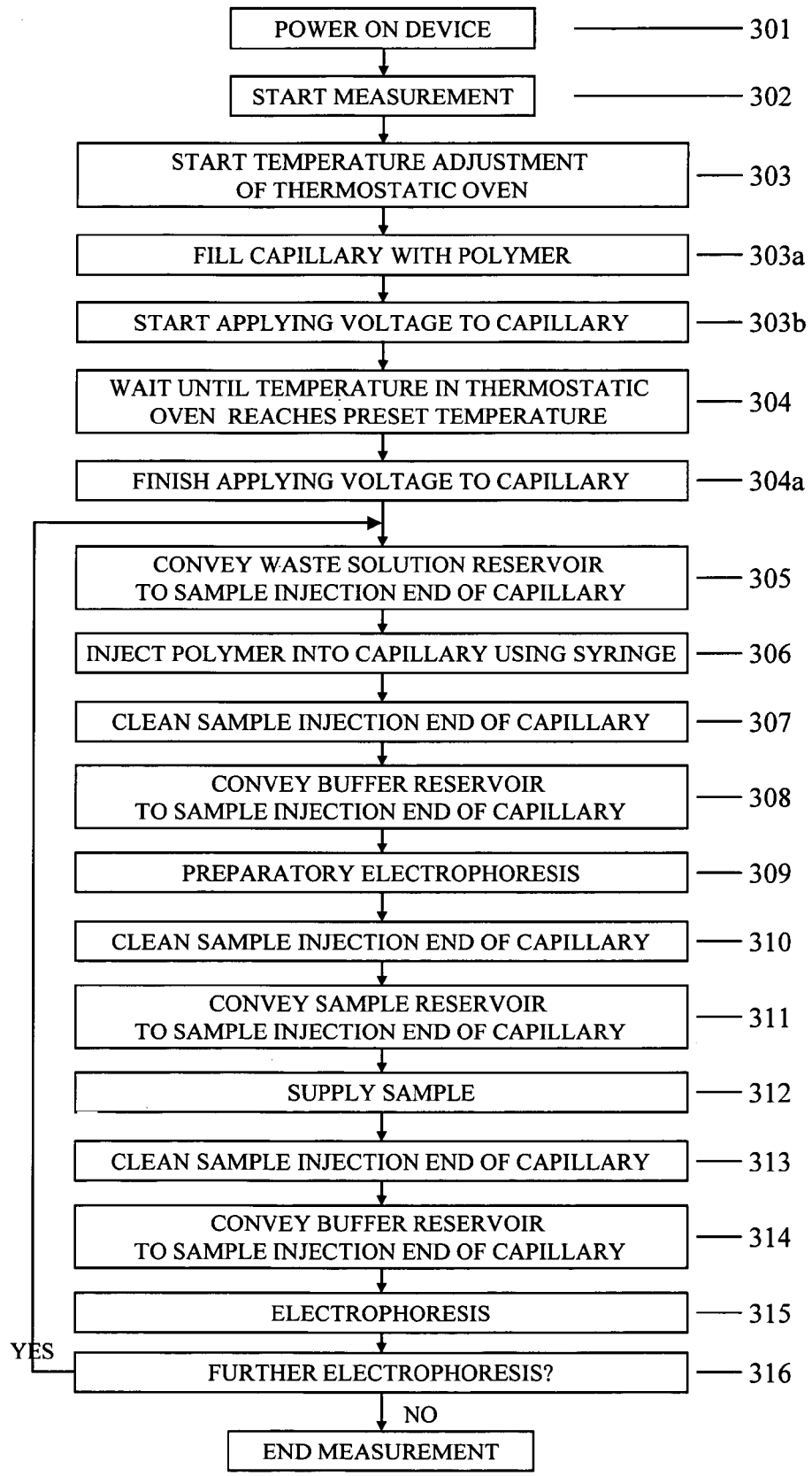
FIG. 3 is a flowchart showing a measurement process according to an embodiment 1.

FIG. 3 is a flowchart for illustrating a measurement operation of a capillary electrophoresis device according to an embodiment 1 in the case where a voltage is applied to a capillary during preheating of a thermostatic oven before the measurement is started. The device is activated (301), the measurement is started (302), and then, the temperature adjustment of the thermostatic oven is started (303). At the same time, or approximately at the same time, the capillary is filled with a polymer, which serves as a separation medium, (303a), a buffer is put back into the capillary, and then, a voltage is applied to the capillary (303b). The process is suspended until the temperature in the thermostatic oven reaches a preset temperature (304). When the temperature in the thermostatic oven reaches the preset temperature, the voltage application is ended (304a). After that, the capillary is filled with the polymer again (306), and the normal electrophoresis process is conducted.

Figure 4:
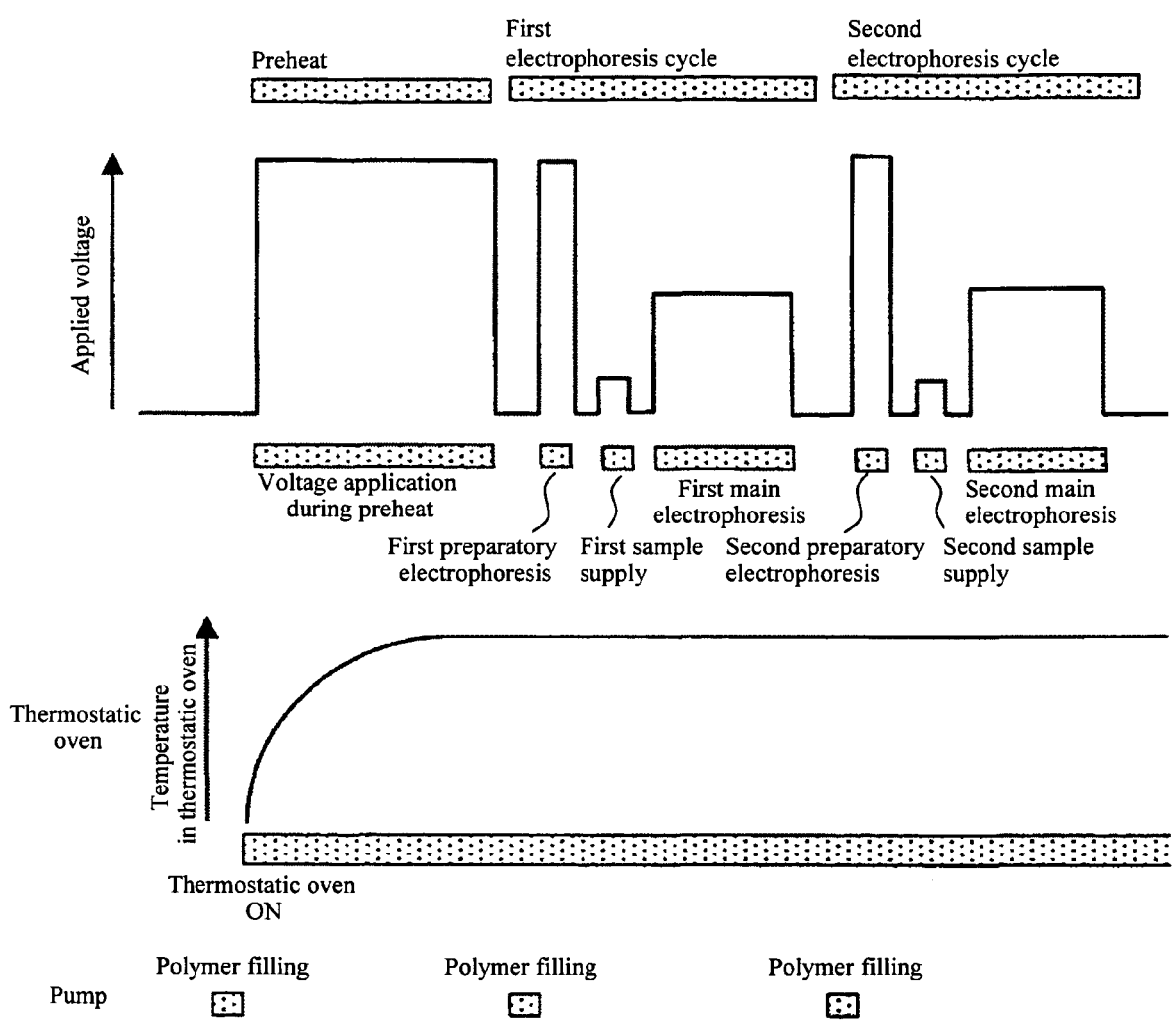
FIG. 4 is a time chart for illustrating successive capillary electrophoresis cycles according to the embodiment 1.

FIG. 4 is a time chart for illustrating successive capillary electrophoresis cycles, which shows variations in voltage, the condition of the thermostatic oven and the pump for charging the polymer, and variations in temperature of the thermostatic oven in the case where a voltage is applied to the capillary during preheating of the thermostatic oven before the measurement is performed. According to prior art, the temperature adjustment of the thermostatic oven is first started, and an electrophoresis is made to occur after the temperature in the thermostatic oven is stabilized. However, according to this embodiment, approximately at the same time as the start of the temperature adjustment of the thermostatic oven, the capillary is filled with the polymer. In parallel with the preheating of the thermostatic oven, a voltage is applied to the capillary. When the preheating is completed, the voltage application is temporarily ended. Then, normal successive electrophoresis cycles are performed.

In the embodiment described above, the preheating is started immediately after the power supply is turned on. However, the preheating may not be started immediately after the power supply is turned on.

The preheating step to raise the temperature in the thermostatic oven to the preset temperature is essential for the electrophoresis. Since the voltage application is performed at the same time as the preheating, no additional time is required, and the electrophoresis process can be performed in the same time as the prior art process.

FIG. 5 includes graphs showing the migration time in cases where the voltage is not applied to the capillary during the preheating of the thermostatic oven and where the voltage is applied to the capillary during the preheating of the thermostatic oven. FIG. 5(A) is a graph showing the migration time in the case where no voltage is applied to the capillary during the preheating of the thermostatic oven. FIG. 5(B) is a graph showing the migration time in the case where a voltage is applied to the capillary during the preheating of the thermostatic oven.

The device used is the Genetic Analyzer 3100 manufactured by the Applied Biosystems Inc (United States). The temperature in the thermostatic oven is set at 60 degrees C., and the preheating time is 30 minutes. The voltage applied during the preheating is 15 kV. The preparatory electrophoresis is conducted for 3 minutes by applying a voltage of 15 kV to the capillary. The applied voltage for the main electrophoresis is 13.2 kV. The sample used is a size standard sample manufactured by the Applied Biosystems Inc (United States), and the time during which the peak of the 700 base length (700b) is detected is regarded as the migration time for 700b.

In the case [601] where no voltage is applied to the capillary during the preheating of the thermostatic oven, the migration times for the first and second electrophoresis cycles are longer than the substantially constant migration times for the third and the following electrophoresis cycles by about 0.8 minutes and about 0.5 minutes, respectively. However, in the case [602] where the voltage is applied to the capillary during the preheating of the thermostatic oven, the migration time for the first electrophoresis cycle is longer than the migration time for the third electrophoresis cycle only by about 0.1 minutes, and the migration times for the second and the following electrophoresis cycles are substantially constant.

According to this embodiment, the migration time for the first electrophoresis cycle can be made equivalent to those for the second and the following electrophoresis cycles. Thus, the data for the first electrophoresis cycle is improved in reliability and can be used, so that time can be saved.

Embodiment 2

In an embodiment 2, the thermostatic oven is preheated to a temperature higher than the temperature during electrophoresis, in order to raise the temperature of the capillary, the buffer and the like to the steady temperature for the successive electrophoresis cycles as fast as possible. During electrophoresis, the capillary itself generates heat, and therefore, the temperature in the capillary is higher than the temperature in the thermostatic oven. Therefore, if the thermostatic oven is preheated to a temperature higher than the preset temperature for electrophoresis, the temperature of the capillary also reaches a temperature close to that for the successive electrophoresis cycles, and therefore, the elongation of the migration time for the first electrophoresis cycle can be reduced without applying a voltage to the capillary. Of course, as in the embodiment 1, a voltage can be applied to the capillary.

Figure 6:
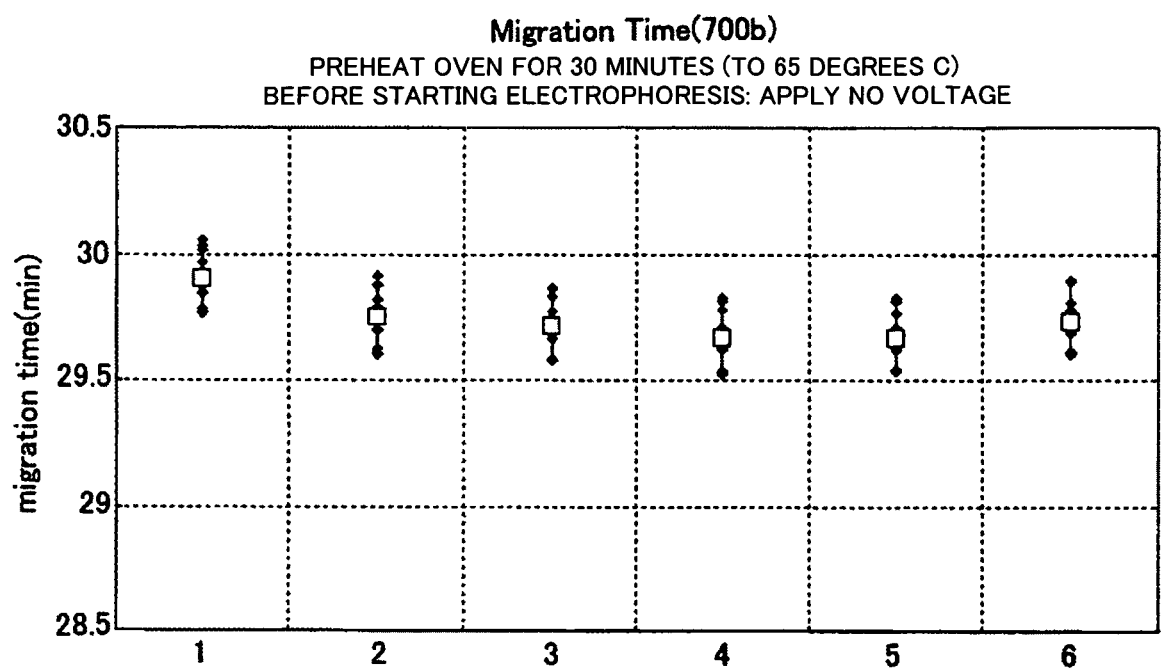
FIG. 6 includes graphs showing the migration time for successive electrophoresis cycles according to an embodiment 2.

FIG. 6 is a graph showing the migration time for successive electrophoresis cycles in the case where the thermostatic oven is preheated to a temperature higher than that for electrophoresis. The graph shows a case where the thermostatic oven is preheated to 65 degrees C. and then set at 60 degrees C. when starting the electrophoresis cycles, and the electrophoresis cycles are started after the temperature is stabilized. The electrophoresis conditions are the same as those in the embodiment 1 under which the data shown in FIG. 5 is obtained. The difference between the migration time for the first electrophoresis cycle and the third electrophoresis cycle is about 0.2 minutes, and the migration times for the second and the following electrophoresis cycles are substantially constant.

The values of the experimental parameters in the embodiments 1 and 2 are only for illustrative purposes, and the measurement can be performed by using other values. Furthermore, the sequence described above can be partially changed.

Embodiment 3

In an embodiment 3, the polymer is preheated to the same temperature as the temperature in the capillary during electrophoresis. If there is a possibility that the polymer is modified by heat, only a small amount of polymer enough for one to several electrophoresis cycles is desirably heated. Filling the capillary with the heated polymer allows the temperature of the capillary to be brought close to the steady temperature for the successive electrophoresis cycles and the elongation of the migration time for the first electrophoresis cycle to be reduced.

What is claimed is:

1. An electrophoresis device, comprising:
   a capillary capable of being filled with a separation medium;
   a thermostatic oven that houses at least a part of the capillary and adjusts the temperature of the capillary; and
   a power supply mechanism capable of applying a voltage at least between the opposite ends of the capillary,
   wherein said power supply mechanism applies a voltage to the separation medium filling said capillary during preheating of the thermostatic oven.

2. The electrophoresis device according to claim 1, wherein the temperature of the thermostatic oven during preheating is higher than the temperature of the thermostatic oven during electrophoresis analysis.

3. The electrophoresis device according to claim 1, further comprising:
   a separation medium filling mechanism capable of filling the capillary with the separation medium,
   wherein the capillary is filled with a preheated separation medium during preheating of the thermostatic oven.

4. The electrophoresis device according to claim 1,
   wherein the temperature of the thermostatic oven during preheating is higher than the temperature of the thermostatic oven during electrophoresis analysis.

5. An electrophoresis method, comprising:
   a step of preparing a capillary that is filled with a separation medium and at least a part of which is housed in a thermostatic oven;
   a step of applying a voltage to the separation medium filling the capillary during preheating of the thermostatic oven; and
   a step of performing an electrophoresis analysis after the temperature in the thermostatic oven reaches a temperature suitable for the electrophoresis analysis.

* * * * *